United States Patent [19]

Hagan

[11] Patent Number: 5,427,772
[45] Date of Patent: Jun. 27, 1995

[54] METHOD FOR ENHANCING HUMAN SKIN ELASTICITY BY APPLYING OCTANOYL LACTYLIC ACID THERETO

[75] Inventor: Desmond B. Hagan, South Wirral, United Kingdom

[73] Assignee: Elizabeth Arden Co., Division of Conopco, Inc., New York, N.Y.

[21] Appl. No.: 141,150

[22] Filed: Oct. 21, 1993

[30] Foreign Application Priority Data

Oct. 23, 1992 [GB] United Kingdom ............... 9222335

[51] Int. Cl.$^6$ .................. A61K 7/40; A61K 7/42; A61K 7/48
[52] U.S. Cl. ................................ 424/59; 424/47; 424/60; 424/69; 514/770; 514/844; 514/846; 514/847; 514/938
[58] Field of Search ................ 424/59; 514/847

[56] References Cited

U.S. PATENT DOCUMENTS

| | | | |
|---|---|---|---|
| 3,098,795 | 7/1963 | Kreps | 424/68 |
| 3,472,940 | 10/1969 | Osipow et al. | 424/70 |
| 3,728,447 | 4/1973 | Osipow et al. | 424/70 |
| 4,184,978 | 1/1980 | France et al. | 252/309 |
| 4,198,311 | 4/1980 | France et al. | 252/117 |
| 4,946,832 | 8/1990 | Goode et al. | 424/70 |
| 5,045,308 | 9/1991 | Spiegel et al. | 424/59 |

FOREIGN PATENT DOCUMENTS

| | | | |
|---|---|---|---|
| 0194097 | 9/1986 | European Pat. Off. | 424/70 |
| 0278370 | 8/1988 | European Pat. Off. | 424/70 |
| 0442708 | 8/1991 | European Pat. Off. | 424/70 |
| WO88/06880 | 9/1988 | WIPO . | |

OTHER PUBLICATIONS

Chemical Abstracts, 1980, vol. 94(2): 7595X Syder.
Chemical Abstracts, 1978, vol. 89(14): 117515a.
British Search Report GB 9222335.3 No date.
Chemical Abstracts vol. 110, 1989, p. 390.
Baiocchi et al. "Use of acyl lactylates in cosmetics and toiletries" Cosmetics and Perfumery *90*, pp. 31–34 (1975).
Osipow et al. "Fatty Acid Lactylates" Drug Cosmet. Ind., May 1969, 64 ff.
L. J. Murphy, "Sorption of acyl lactylates by hair and skin as documented by radio tracer studies" Cosmetics and Toiletries *94*, 43 ff. (1979).
Serna-Saldivar et al., "Effect of Sodium Stearoyl -2-2-Lactylate on the Rheological and Baking Properties of Wheat Bread Fortified with Defatted Soybean and Sesame Meal" Journal of Food Science, vol. 53, No. 1 (1988), pp. 211–214, 230.

*Primary Examiner*—Dale R. Ore
*Attorney, Agent, or Firm*—Milton L. Honig

[57] ABSTRACT

The use of acyl lactylates having a $C_4$ to $C_{16}$ acyl group or of compositions containing such acyl lactylates to enhance the elasticity of skin, is provided.

2 Claims, No Drawings

METHOD FOR ENHANCING HUMAN SKIN ELASTICITY BY APPLYING OCTANOYL LACTYLIC ACID THERETO

FIELD OF INVENTION

The invention relates to the use of specific acyl lactylates as skin elasticity enhancing agents. In particular, the invention is concerned with the use of these acyl lactylates to increase the elasticity of the stratum corneum of the skin.

BACKGROUND OF THE INVENTION

A soft, supple and flexible skin has a marked cosmetic appeal and is an attribute of normal functioning epidermis. The outer layer of the epidermis, i.e. the stratum corneum, can however become inelastic and hard or flaky following exposure to adverse climate conditions. This can also be caused by excessive contact with detergents or solvents which result in a loss of skin moisture. Consequently, the skin loses its soft, supple and flexible characteristics.

It is therefore apparent that there exists a need for an effective treatment for skin which has become relatively inelastic and inflexible.

In an article of F Baiocchi, D Jennings and A J Del Vecchio in Cosmetics and Perfumery 90, 31–34 (1975) it is alleged that sodium stearoyl lactylates when incorporated in a hand cream or lotion result in a subjectively smooth and supple but not excessively greasy feeling when such creams or lotions are topically applied to the hands. The main reason for including these lactylates in hand and body cream formulations is that they act as very efficient emulsifiers.

In an article by L I Osipow et al in Drug Cosmet Ind, May 1969, 64 ff. it is disclosed that sodium stearoyl lactylate may be used in oil-in-water cosmetic creams as the emulsifier to impart body, lubricity and a pearlescent opacity to the cream. It is alleged that its absorption to the skin may enhance its softening action.

In another article by L J Murphy in Cosmetics and Toiletries 94, 43 ff (1979) the absorption of acyl lactylates on the skin was examined by using pig skin as a model. It is described that sodium isostearoyl lactylate (ISL) appears to reduce dryness and scaling of skin and restores a healthy texture to dry skin.

EP-B-278 370 (Kao) discloses specific acyl lactylates having alpha-branched acyl groups. This type of acyl lactylates is used in hair rinses and hair shampoos for their good hair conditioning action.

EP-A-442 708 (Unilever) discloses cosmetic compositions containing 2hydroxy alkanoic acids. Due to the presence of these acids in the compositions, several benefits are imparted to the skin, such as an increase in the elasticity of the skin, particularly of the stratum corneum. Similarly, EP-B-7 785 (Unilever) discloses cosmetical compositions comprising 2-hydroxy alkanoic acids, which also give various skin benefits when topically applied to the skin.

However, the extent to which the elasticity of skin can be enhanced by using these conventional actives is not satisfactory. Therefore, we have searched for other more effective actives. These actives should also be functional at pH values close to neutral which is often not the case with conventional skin elasticity increasing agents, eg. 2-hydroxy alkanoic acids, which require fairly acidic pH values to have a reasonable shelf life.

It has now been discovered that a narrow range of short chain acyl lactylates is able to provide these desired properties. Surprisingly, these acyl lactylates are capable of enhancing the elasticity of skin to a much greater extent than conventional actives when applied to the skin.

DEFINITION OF THE INVENTION

Accordingly, the invention provides, for use as a skin elasticity enhancing agent, one or more acyl lactylates of the following structure (1)

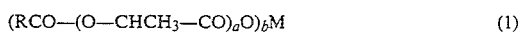

$$(RCO-(O-CHCH_3-CO)_aO)_bM \qquad (1)$$

where RCO represents a $C_4$ to $C_{16}$ acyl group; M represents H or a cosmetically-acceptable counterion having a valency of 1 or 2; a is an integer of from 1 to 4; and b is 1 or 2.

DISCLOSURE OF THE INVENTION

The invention is accordingly concerned with the use of acyl lactylates having the structure (1) as defined above to enhance the elasticity of skin, in particular the elasticity of the outer layer of the epidermis, namely the stratum corneum. Evidence for the superiority of the specific acyl lactylates used according to the invention compared with conventional agents is given later herein.

The acyl lactylates of the structure (1) are preferably those where RCO represents a $C_8$ to $C_{14}$ acyl group, more preferably a $C_8$ to $C_{12}$ acyl group and most preferably a $C_8$ acyl group.

If M in structure (1) in a counterion, then it is preferably chosen from alkali metal cations, alkaline earth metal cations, ammonium or substituted ammonium having one or more $C_1$ to $C_3$ alkyl or hydroxy alkyl groups However, it is preferred that the acyl lactylates are used in form of their free acids, that is to say that M in structure (1) is hydrogen.

Examples for preferred acyl lactylates having the above structure (1), include:
Lauroyl dilactylic acid
n-Octanoyl lactylic acid

COSMETICALLY ACCEPTABLE VEHICLE

It is preferred to incorporate the acyl lactylate in a cosmetical acceptable vehicle to form a composition which is then topically applied to the skin.

Vehicles other than water may include liquid or solid emollients, propellants solvents, humectants, thickeners and powders. Examples of each of these types of vehicles which can be used singularly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as polydimethylsiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, decyl oleate, myristyl myristate;

Propellants, such a propane, butane, isobutane, dimethyl ether, carbon dioxide, nitrous oxide;

Solvents, such as ethyl alcohol, isopropanol, acetone, ethylene glycol monoethyl ether, diethylene glycol monobutyl ether, diethylene glycol monoethyl ether, dimethyl sulphoxide;

Powders, such as chalk, talc, fullers earth, kaolin, starch, gums, colloidal silica, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

A preferred vehicle is a water-in-silicon oil emulsion. Examples for suitable silicone oils are available from Dow Corning under the trade names DC 344 and DC 3225C.

The cosmetically acceptable vehicle will usually form from 10 to 99.9%, preferably from 50 to 99% by weight of the composition, and can, in the absence of other cosmetic adjuncts form the balance of the composition. If the acyl lactylate is combined with a cosmetically acceptable vehicle to form a cosmetic composition, then the composition should preferably have a pH value in the range of 3 to 8 and more preferably 4 to 7.

Adjustment of the pH value of the composition can be achieved by addition of a pH adjustant as conventionally used in cosmetic compositions.

COSMETIC ADJUNCTS

The aforementioned composition comprising the acyl lactylate and a cosmetically acceptable vehicle can in addition optionally comprise cosmetic adjuncts. Example for suitable cosmetic adjuncts are as follows:

Organic sunscreen materials in an amount of from 0.1 to 20%, preferably from 1 to 10% by weight;

Inorganic sunscreens, such as ultra fine titanium dioxide;

Emulsifiers, these are present if the composition for the use according to the invention is in the form of an emulsion in which case an oil or oily material will normally be present, together with an emulsifier to provide either a water-in-oil emulsion or an oil-in-water emulsion. The amount of the emulsifier of mixtures thereof will normally be from 1 to 50%, preferably from 2 to 20% and most preferably from 2 to 10% by weight of the composition.

Surfactants, such as anionic, non-anionic or amphotoric surfactants or mixtures thereof, particularly when the composition is intended for use when bathing or in the shower. When present the surfactants form from 2 to 40% by weight and preferably from 5 to 30% by weight.

Other Cosmetic Adjuncts, which include for instance antioxidants, such as butyl hydroxy toluene; humectants such as glycerol, sorbitol; buffers such as lactic acid or sodium hydroxide; waxes such as beeswax, paraffin wax; plant extracts, such as aloa vera; thickeners; colourants; and perfumes.

The acyl lactylates can be provided in a wide variety of compositions intended for topical application to skin. These compositions can, for example, include skin creams, lotions, milks and powder as well as skin cleansing products. The skin elasticity enhancing effect is provided by topically applying the acyl lactylates or preferably compositions containing the acyl lactylates to the desired area of the skin.

SKIN ELASTICITY ENHANCING EFFECT OF THE ACYL LACTYLATE

The plasticising effect imparted to the skin by using the acyl lactylates as herein defined was assessed by measuring the increase in extensibility of isolated stratum corneum samples subsequent to application of compositions containing such acyl lactylates.

MEASURING THE EXTENSIBILITY OF ISOLATED STRATUM CORNEUM

Stratum corneum is obtained from the rear feet of guinea pigs. The footpads were immersed in water at 60° C. for 2–3 minutes, after which the epidermis was readily separated from the dermis. The Malpighian cells were not removed as their presence did not influence subsequent extensibility measurements. Exposure to trypsin, urea and non-aqueous solvent was regarded as unacceptable and avoided. The samples of stratum corneum were thoroughly dried with filter paper cut into rectangular strips approximately 2 mm wide and 15 to 20 mm long with a stainless steel punch.

The extensibility was measured using an extensometer. Measurements were made on strips of stratum corneum which were clamped vertically, attached to a fixed load cell above and to a motor driven clamp below. The linear rate of stretch was 0.01 mm s$^{-1}$. A chart recorder monitored the output of the load cell against time. As the strips were stretched the load cells was subjected to an increasing load. Because of the uniform rate of stretch the record provided a curve of deformation against load. The whole apparatus was enclosed in a sealed perspex box in which the relative humidity and temperature were controlled and normally constant at 65% RH ±3% and 20° C. ±1° C. This humidity level was chosen to minimise the effect of moisture. At lower humidity the samples would have been expected to become brittle. At higher humidity, softening through moisture uptake could have concealed other effects.

EXPERIMENT I

Acyl Lactylate—Containing Solutions

The following experiments compare the extensibility of the stratum corneum when treated either with the acyl lactylates according to the invention or with certain other conventionally used skin-plasticising agents, such as 2-hydroxy octanoic acid and lactic acid.

For each experimental procedure, six strips of guinea-pig footpad epidermis were immersed in water for 3 hrs at 20°, blotted dry, and allowed to equilibrate overnight at 20° C. and 65% RH. The extensibility of each was measured and expressed as % extension per 100 g load (of the original length at controlled RH) from the most linear portion of the load-deformation curve.

The strips were then immersed in an aqueous solution of the test material for 3 hrs at 20° C., blotted dry and equilibrated overnight at 20° C. and 65% RH. After remeasuring extensibility, the efficacy was expressed as the mean ratio (±2 standard errors) of extensibility after test solution exposure to extensibility after water treatment.

The test solutions employed for treating the samples of stratum corneum were 0.06M and 0.12M aqueous solution of all test substances adjusted to a pH value of 4 by using dilute HCl or dilute NaOH, respectively.

The results are set out in Table 1 below.

TABLE 1

| Compound | EXTENSIBILITY RATIO 0.06M |
|---|---|
| Hexanoyl Lactylic acid | 1.36 ± 0.07 |
| Octanoyl Lactylic acid | 2.36 ± 0.59 |
| Pationic 122A*1 | 1.98 ± 0.55 |
| Pationic 138C*2 | 1.44 ± 0.38 |
| Sodium stearoyl lactylate (Crolactil SSL) | 1.24 ± 0.28 |
| (2-hydroxy octanoic acid) | 1.30 ± 0.27 |
| Lactic Acid | 1.42 ± 0.13 |

*1 mixture of sodium capryl/sodium lauroyl lactylate (50:50 w/w)
*2 mixture of sodium lauroyl/sodium myristoyl lactylate (70:30 w/w)

The above data clearly show the superiority of the acyl lactylate used in the present invention, compared with the conventionally used acyl lactylate, namely sodium stearoyl lactylate, and other actives, namely 2-Hydroxy octanoic acid and lactic acid, which both are known for their skin plasticising effect.

An especially high extensibility ratio was obtained for Octanoyl lactylic acid and therefore acyl lactylates having a $C_8$ acyl group are the most preferred lactylates used according to the invention.

EXPERIMENT 2

Acyl Lactylates—Containing Skin Cream

This experiment compares the extensibility enhancing effect of two skin creams containing (a) Octanoyl lactylic acid and (b) 2-Hydroxy octanoic acid together with lactic, respectively.

The respective extensibility ratio was measured using the method as described above with the exception that the test creams were applied to the stratum corneum sample by the following rub-in procedure.

The rub-in procedure consisted of five separate applications of 0.2 ml test creme to each sample of stratum corneum. Each application lasted 60 seconds with one hour between each application. The creams were applied manually by gently rubbing together the thumb and forefinger protected by a rubber glove. One hour after the last of the five applications, each sample of stratum corneum was blotted between sheets of paper tissue and left to equilibrate for 24 h at 60% relative humidity and 20° C. before carrying out the extensibility measurement.

The exact formulations of the test creams were as follows:

| Formulation of Water-in-Silicone Creams | | |
|---|---|---|
| | % w/w | |
| INGREDIENT | Cream 1 | Cream 2 |
| Butane-1,3-diol | 10.00 | 10.00 |
| Silicone Oil (DC 344) | 8.20 | 8.20 |
| Silicone Oil (DC 3225C) | 12.00 | 12.00 |
| Methylparaben | 0.20 | 0.20 |
| Propylparaben | 0.10 | 0.10 |
| TiO2 (Tiona AG) | 0.20 | 0.20 |
| Petroleum Jelly | 0.50 | 0.50 |
| Mineral Oil | 1.50 | 1.15 |
| Perfume | 0.15 | 0.15 |
| Sodium Chloride | 2.00 | 2.00 |
| Octanoyl Lactylic Acid | — | 1.00 |
| 2-Hydroxy octanoic acid | 1.00 | — |
| Lactic Acid | 5.00 | — |

-continued

| Formulation of Water-in-Silicone Creams | | |
|---|---|---|
| | % w/w | |
| INGREDIENT | Cream 1 | Cream 2 |
| Bronopol (2-Bromo-2-nitropropane-1,3-diol) | 0.01 | — |
| BHT (Butyl hydroxy toluene) | 0.05 | — |
| Sodium Hydroxide | — | to pH 6.05 |
| Triethanolamine | to pH 4.5 | — |
| Demineralised Water | to 100.00 | to 100.0 |

The extensibility ratios obtained by using the above mentioned creams are set out in Table II below.

TABLE 2

| | ACTIVE | pH | EXTENSIBILITY RATIO |
|---|---|---|---|
| Cream 1 | 2-Hydroxy octanoic acid + lactic acid | 4.5 | 3.36 ± 0.58 |
| Cream 2 | Octancyl lactylic acid | 6.05 | 5.44 ± 0.95 |

The above results show that an amount of as little as 1% by weight Octanoyl lactylic acid is much more effective compared with a combination of 1% by weight 2-Hydroxy octanoic acid and 5% by weight lactic acid, even when the latter product is formulated at a lower pH. The invention is further illustrated by the following examples of compositions incorporating the acyl lactylates.

EXAMPLES

| Ingredients | % w/w |
|---|---|
| Example 1 - Water-in-oil skin cream | |
| Silicone oil | 20.00 |
| Sodium chloride | 2.00 |
| Sodium octanoyl lactylate | 1.00 |
| Whitener | 0.15 |
| Preservatives | 0.36 |
| Sodium hydroxide | 1.00 |
| Water | to 100.00 |
| Example 2 - Water-in-oil skin cream | |
| Silicones | 20.50 |
| Whitener | 0.20 |
| Preservatives | 0.30 |
| Perfume | 0.15 |
| Ammonium hydroxide | 7.95 |
| Decanoyl lactylic acid | 1.00 |
| Humectant | 10.00 |
| Ammonium chloride | 2.00 |
| Water | to 100.00 |
| Example 3 - Water-in-oil skin cream with sunscreens | |
| Silicones | 24.00 |
| Whitener | 0.10 |
| Preservatives | 0.01 |
| Potassium lauroyl lactylate | 1.50 |
| Potassium chloride | 1.50 |
| Humectants | 5.00 |
| Evening primrose oil | 3.00 |
| Sunscreens | 4.00 |
| Bactericides | 0.30 |
| Water | to 100.00 |
| Example 4 - Oil-in water skin cream | |
| Emulsifier | 10.00 |
| Silicone oil | 8.00 |
| Thickener | 0.50 |
| Whitener | 0.20 |
| Preservatives | 0.10 |
| Octanoyl lactylic acid | 2.00 |
| Humectant | 10.00 |
| Evening primrose oil | 2.00 |
| Sunscreens | 3.00 |
| Bactericides | 0.30 |

| Ingredients | % w/w |
| --- | --- |
| Triethanolamine | 3.10 |
| Water | to 100.00 |
| Example 5 - Face mask | |
| Kaolin | 35.00 |
| Bentonite | 5.00 |
| Cetyl alcohol | 2.00 |
| Potassium myristoyl lactylate | 5.25 |
| Glycerol | 10.00 |
| Methyl paraben | 0.10 |
| Potassium dodecyl sulphate | 2.00 |
| Perfume | 0.75 |
| Water | to 100.00 |

I claim:

1. A method of enhancing the elasticity of human skin comprising applying topically to the skin an effective amount of a cosmetic composition comprising an acyl lactylate of the structure (1):

$$(RCO-(O-CHCH_3-CO)_aO)_bM \qquad (1)$$

where RCO represents a $C_8$ acyl group; M represents H or a cosmetically-acceptable counterion selected from the group consisting of alkali metal cation, alkaline earth metal cation, ammonium cation, an ammonium cation having at least one $C_1$ to $C_3$ alkyl and an ammonium cation having at least one $C_1$ to $C_3$ hydroxy alkyl group; a is an integer of from 1 to 4; and b is 1 or 2; together with a cosmetically acceptable vehicle.

2. The method of claim 1, wherein the composition comprises from about 0.1 to about 10% by weight of the acyl lactylate.

* * * * *